United States Patent
Nagamori et al.

(10) Patent No.: US 8,163,179 B2
(45) Date of Patent: Apr. 24, 2012

(54) APPARATUS FOR REMOVING DISSOLVED HYDROGEN SULFIDE IN ANAEROBIC TREATMENT

(75) Inventors: Yasuhiko Nagamori, Fuchu (JP); Takumi Obara, Fuchu (JP); Nobuyuki Ashikaga, Kawasaki (JP); Hiroshi Tamura, Tokyo (JP); Toshiharu Ishihara, Yokohama (JP); Takayuki Ishige, Yokohama (JP); Miyuki Momiji, Mitaka (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 320 days.

(21) Appl. No.: 12/528,897

(22) PCT Filed: Dec. 12, 2008

(86) PCT No.: PCT/JP2008/072616
§ 371 (c)(1),
(2), (4) Date: Aug. 27, 2009

(87) PCT Pub. No.: WO2009/084405
PCT Pub. Date: Jul. 9, 2009

(65) Prior Publication Data
US 2010/0101985 A1 Apr. 29, 2010

(30) Foreign Application Priority Data
Dec. 27, 2007 (JP) .................... 2007-337807

(51) Int. Cl.
*C02F 3/28* (2006.01)
(52) U.S. Cl. ...................... 210/259; 210/603
(58) Field of Classification Search .............. 210/603, 210/605, 620, 630, 252, 259
See application file for complete search history.

(56) References Cited

U.S. PATENT DOCUMENTS

| | | | | |
|---|---|---|---|---|
| 4,354,936 A | * | 10/1982 | Ishida et al. | 210/603 |
| 5,958,238 A | * | 9/1999 | Langerwerf | 210/603 |
| 7,060,233 B1 | * | 6/2006 | Srinivas et al. | 423/210 |
| 2007/0175822 A1 | * | 8/2007 | Kamachi et al. | 210/603 |

FOREIGN PATENT DOCUMENTS

JP 2-26615 1/1990
(Continued)

OTHER PUBLICATIONS

International Preliminary Report on Patentablity (IPRP) and Written Opinion of the International Searching Authority mailed Jul. 29, 2010, in corresponding International Application No. PCT/JP2008/072616.

(Continued)

*Primary Examiner* — Fred Prince
(74) *Attorney, Agent, or Firm* — Finnegan, Henderson, Farabow, Garrett & Dunner, L.L.P.

(57) ABSTRACT

Disclosed is an apparatus for removing dissolved hydrogen sulfide, including an anaerobic treatment tank (1) that anaerobically treats organic discharged water, a circulation water tank (3), means for introducing organic discharged water into circulation water, a treated-water tank (4) that temporarily stores anaerobically treated water, a biological desulfurization tower (5) that desulfurizes biogas formed by anaerobic treatment, air feeding means for feeding air to the biological desulfurization tower (5), water feeding means for feeding water to the biological desulfurization tower (5), first aerating means (9*a*) for blowing a part of biologically desulfurized gas from the biological desulfurization tower (5), into the treated-water tank (4), and second aerating means (9*b*) for blowing exhaust gas discharged from the treated-water tank (4) into a solution circulating between the anaerobic treatment tank (1) and circulation water tank (3).

7 Claims, 5 Drawing Sheets

FOREIGN PATENT DOCUMENTS

| | | |
|---|---|---|
| JP | 3-270792 | 12/1991 |
| JP | 7-16593 | 1/1995 |
| JP | 7-16594 | 1/1995 |
| JP | 7-148495 | 6/1995 |
| JP | 2005-262182 | 9/2005 |

OTHER PUBLICATIONS

International Search Report from the Japanese Patent Office for International Application No. PCT/JP2008/072616 (Jan. 27, 2009).

* cited by examiner

APPARATUS FOR REMOVING DISSOLVED HYDROGEN SULFIDE IN ANAEROBIC TREATMENT

CROSS REFERENCE TO RELATED APPLICATIONS

This application is a national phase application based on PCT/JP2008/072616 (not published in English), filed Dec. 12, 2008, which claims the priority of Japanese Application No. 2007-337807, filed Dec. 27, 2007, the content of both of which is incorporated herein by reference in their entirety.

TECHNICAL FIELD

The present invention relates to an apparatus for removing dissolved hydrogen sulfide in an anaerobic treatment.

BACKGROUND ART

As is well-known, an anaerobic treatment method is known as a method of cleaning organic discharged water such as sewage and industrial effluent. In the anaerobic treatment method, organic matter is decomposed by the action of anaerobic microorganisms. Biogas containing methane, carbon dioxide and hydrogen sulfide is formed as a byproduct. The biogas can be utilized as fuel in gas boilers, etc. after hydrogen sulfide in the gas is removed (desulfurized). However, it has become a problem that because the formed hydrogen sulfide remains dissolved in the liquid phase in an anaerobic treatment tank, anaerobically treated water releases a bad smell. In addition, hydrogen sulfide may inhibit the activity of anaerobic microorganisms, which causes a reduction in the efficiency of a drainage treatment.

As a conventional method of removing hydrogen sulfide dissolved in anaerobically treated water, a method which includes blowing air into an anaerobic treatment tank (for example, Jpn. Pat. Appln. KOKAI Publication No. 7-16594) is known. As a method of removing hydrogen sulfide dissolved in an anaerobic reaction tank, Jpn. Pat. Appln. KOKAI Publication No. 7-16593, for example, is known. This method is a method which includes circulating a part of the treated water in a closed balancing tank between a closed anaerobic reaction tank and the balancing tank, to remove hydrogen sulfide from fermentation gas in the gas phase in either the reaction tank or the balancing tank, and then aerating the liquid phase in either the reaction tank or the balancing tank.

As a desulfurization method, a biological desulfurization method is also known. In this biological desulfurization method, hydrogen sulfide is removed from biogas by oxidization by the action of sulfur-oxidizing bacteria. The microorganisms are fed a nutritive salt-containing water so that they grow. This water also has a role in absorbing hydrogen sulfide from biogas and discharging a product formed by oxidization of hydrogen sulfide. In biological desulfurization, air is usually fed as the oxygen necessary for oxidization.

DISCLOSURE OF INVENTION

An object of the present invention is to provide an apparatus for removing dissolved hydrogen sulfide in anaerobic treatment capable of reducing hydrogen sulfide dissolved in an anaerobic treatment tank, in cases where biological desulfurization is used as a method of desulfurizing biogas formed in an anaerobic digester tank.

An apparatus for removing dissolved hydrogen sulfide in anaerobic treatment according to a first aspect of the present invention comprises:

an anaerobic treatment tank that anaerobically treats organic discharged water;

a circulation water tank that circulates a solution between itself and the anaerobic treatment tank by a circulation pump;

means for introducing organic discharged water into circulation water circulating between the anaerobic treatment tank and the circulation water tank;

a treated-water tank that temporarily stores anaerobically treated water discharged from the circulation water tank;

a biological desulfurization tower that desulfurizes biogas formed by anaerobic treatment;

air feeding means for feeding air to the biological desulfurization tower; water feeding means for feeding water to the biological desulfurization tower;

first aerating means for blowing a part of biologically desulfurized gas from the biological desulfurization tower, into the treated-water tank; and second aerating means for blowing exhaust gas discharged from the treated-water tank, into a solution circulating between the anaerobic treatment tank and the circulation water tank. According to the present invention, there can be provided an apparatus for removing dissolved hydrogen sulfide in anaerobic treatment capable of reducing hydrogen sulfide dissolved in an anaerobic treatment tank, in cases where biological desulfurization is used as a method of desulfurizing biogas formed in an anaerobic digester tank.

BEST MODE FOR CARRYING OUT THE INVENTION

The apparatus for removing dissolved hydrogen sulfide in an anaerobic treatment according to a first aspect of the invention comprises an anaerobic treatment tank that anaerobically treats organic discharged water, a circulation water tank that circulates a solution between itself and the anaerobic treatment tank by a circulation pump, means for introducing organic discharged water into circulation water circulating between the anaerobic treatment tank and the circulation water tank, a treated-water tank that temporarily stores anaerobically treated water discharged from the circulation water tank, a biological desulfurization tower that desulfurizes biogas formed by anaerobic treatment, air feeding means for feeding air to the biological desulfurization tower, water feeding means for feeding water to the biological desulfurization tower, first aerating means for blowing a part of biologically desulfurized gas from the biological desulfurization tower into the treated-water tank, and second aerating means for blowing exhaust gas discharged from the treated-water tank into a solution circulating between the anaerobic treatment tank and the circulation water tank.

In the first aspect of the invention, the second aerating means is aerating means for blowing exhaust gas discharged from the treated-water tank into the circulation water tank. In this case, the apparatus preferably includes means for returning exhaust gas discharged from the circulation water tank to the biological desulfurization tower. In this constitution, a part of treated gas in the biological desulfurization tower is blown into the treated-water tank, its exhaust gas is blown into the circulation water tank, then returned to the biological desulfurization tower. Accordingly, the concentration of dissolved hydrogen sulfide in the liquid phase in the anaerobic treatment tank can be reduced, a reduction in the activity of anaerobic microorganisms by hydrogen sulfide can be prevented, and the anaerobic treatment performance can be kept high. For the same reason, the hydrogen sulfide concentration of anaerobically treated water can be reduced, and the treated water can be prevented from generating a bad smell. The concentration of oxygen remaining in the treated gas in the biological desulfurization tower is reduced, thereby increasing the methane concentration of the treated gas, thus increasing the amount of energy per unit flow volume of biogas.

In the first aspect of the invention, the second aerating means may be aerating means for blowing exhaust gas discharged from the treated-water tank into the anaerobic treatment tank. In this constitution, a part of treated gas in the biological desulfurization tower is blown into the treated-water tank, and its exhaust gas is blown into the anaerobic treatment tank. Accordingly, the anaerobic treatment performance can be kept high, as described above. For the same reason, the treated water can be prevented from generating a bad smell, and the amount of energy per unit flow volume of biogas can be increased.

In the first aspect of the invention, the second aerating means consists of aerating means for blowing exhaust gas discharged from the treated-water tank into the circulation water tank and aerating means for blowing exhaust gas discharged from the circulation water tank into the anaerobic treatment tank. In this constitution, a part of treated gas in the biological desulfurization tower is blown into the treated-water tank, its exhaust gas is blown into the circulation water tank, and exhaust gas from the circulation water tank is further blown into the anaerobic treatment tank. Accordingly, the anaerobic treatment performance can be kept high, as described above. For the same reason, the treated water can be prevented from generating a bad smell, and the amount of energy per unit flow volume of biogas can be increased.

The apparatus for removing dissolved hydrogen sulfide in an anaerobic treatment according to a second aspect of the invention includes an anaerobic treatment tank that anaerobically treats organic discharged water, a circulation water tank that circulates a solution between itself and the anaerobic treatment tank by a circulation pump, means for introducing organic discharged water, into circulation water circulating between the anaerobic treatment tank and the circulation water tank, a biological desulfurization tower that desulfurizes biogas formed by anaerobic treatment, air feeding means for feeding air to the biological desulfurization tower, water feeding means for feeding water to the biological desulfurization tower, means for aerobically treating anaerobically treated water, a sludge storage tank that temporarily stores excessive sludge generated by aerobic treatment, aerating means for blowing a part of biologically desulfurized gas from the biological desulfurization tower, into the sludge storage tank, aerating means for blowing exhaust gas discharged from the sludge storage tank into the circulation water tank, and means for returning exhaust gas discharged from the circulation water tank to the biological desulfurization tower.

The apparatus for removing dissolved hydrogen sulfide in an anaerobic treatment according to a third aspect of the invention includes an anaerobic treatment tank that anaerobically treats organic discharged water, a circulation water tank that circulates a solution between itself and the anaerobic treatment tank by a circulation pump, means for introducing organic discharged water into circulation water circulating between the anaerobic treatment tank and the circulation water tank, a treated-water tank that temporarily stores anaerobically treated water discharged from the circulation water tank, a first biological desulfurization tower that desulfurizes biogas formed by anaerobic treatment, air feeding means for feeding air to the first biological desulfurization tower, water feeding means for feeding water to the first biological desulfurization tower, a second biological desulfurization tower to which treated gas and biogas from the first biological desulfurization tower are sent and which desulfurizes the biogas, water feeding means for feeding water to the second biological desulfurization tower, aerating means for blowing a part of treated gas from the second biological desulfurization tower into the circulation water tank, and means for returning exhaust gas discharged from the circulation water tank to the biological desulfurization tower.

Now, specific examples of the apparatus for removing dissolved hydrogen sulfide in an anaerobic treatment according to the present invention are described in detail by reference to the drawings. However, the present invention is not limited to the following description.

EXAMPLE 1

Figure 1:
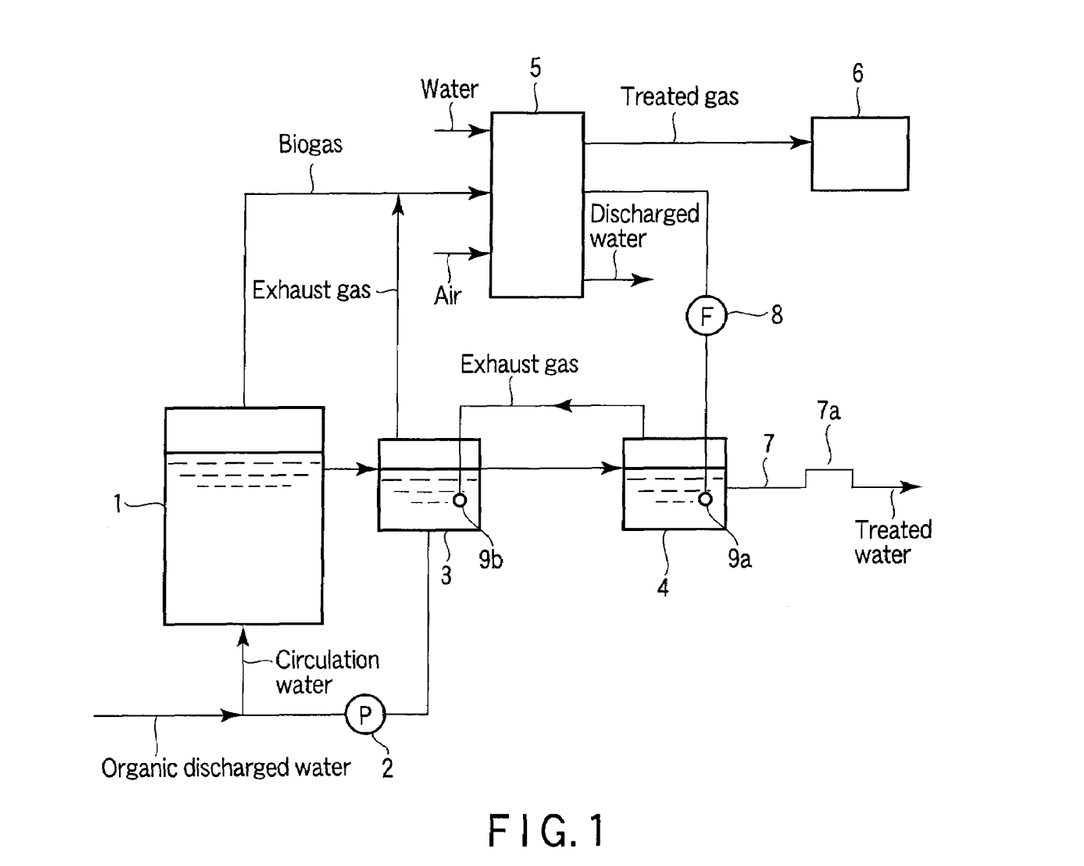
FIG. 1 is a block diagram of the apparatus for removing dissolved hydrogen sulfide in an anaerobic treatment in Example 1 according to the present invention.

FIG. 1 is a schematic block diagram of the apparatus for removing dissolved hydrogen sulfide in an anaerobic treatment in Example 1 according to the present invention.

Numeral 1 in the figure is an anaerobic treatment tank that anaerobically treats organic discharged water. The circulation water tank 3 is connected via a circulation pump 2 to the anaerobic treatment tank 1. A solution (circulation water) is circulated by the circulation pump 2 between the anaerobic treatment tank 1 and circulation water tank 3. Organic discharged water is introduced by introducing means (not shown) into the circulation water circulating between the anaerobic treatment tank 1 and circulation water tank 3. The organic discharged water is introduced into the circulation water in the lower part of the anaerobic treatment tank 1. The organic discharged water is decomposed and cleaned by the action of anaerobic microorganisms held in the anaerobic treatment tank 1. The cleaned treated water passes through the circulation water tank 3, is temporarily stored in a treated-water tank 4 and then released to a river or a sewer. A treated-water drain 7 from the treated-water tank 4 is water-sealed. Numeral 7a in the figure is a water seal portion of the treated-water drain 7.

Biogas formed in the anaerobic treatment tank 1 is sent to a biological desulfurization tower 5 where the biogas is desulfurized. The biological desulfurization tower 5 is supplied with air by air feeding means (not shown) and with water by water feeding means (not shown). In the biological desulfurization 5, hydrogen sulfide is oxidized by the action of sulfur-oxidizing bacteria. The oxidized product together with water is discharged as discharged water. The treated gas after desulfurization is sent to a gas boiler 6 and utilized as fuel. A part of the treated gas from the biological desulfurization tower 5 is blown by fan 8 via an aeration tube (first aerating means) 9a into a treated-water tank 4. Exhaust gas discharged from the treated-water tank 9 is blown via an aeration tube (second aerating means) 9b into a circulation water tank 3. Exhaust gas discharged from the circulation water tank 4 together with biogas from the anaerobic treatment tank 1 is returned via returning means (not shown) to the biological desulfurization tower 5.

Now, the working of the apparatus for removing dissolved hydrogen sulfide in FIG. 1 is described in detail.

The treated gas in the biological desulfurization tower 5 contains no or little hydrogen sulfide, but oxygen not used in the oxidization reaction in the biological desulfurization tower 5 remains therein. Accordingly, when the treated gas is blown into the treated-water tank 4, oxygen in the treated gas is consumed with treated water in an anaerobic state. By sending the exhaust gas from the treated-water tank 4 into the circulation water tank 3, oxygen is not brought into the circulation water tank 3. Neither is oxygen brought by circulation into the anaerobic treatment tank 1. Therefore, the reduction, by oxygen, in the activity of anaerobic microorganisms held in the anaerobic treatment tank 1 can be prevented.

When exhaust gas from the treated-water tank 4 is blown into the circulation water tank 3, hydrogen sulfide dissolved in the circulating liquid phase in the anaerobic treatment tank 1 is removed by emission (stripping) into the gas phase. This is because the concentration of hydrogen sulfide contained in the treated gas is low. The exhaust gas containing emitted hydrogen sulfide from the circulation water tank 3 is mixed with biogas and returned to the biological desulfurization tower 5 where the hydrogen sulfide is removed. The concentration of dissolved hydrogen sulfide in the liquid phase is thereby reduced, thus preventing the treated water from generating a bad smell.

A water seal portion 7a is arranged in a treated-water drain 7 connected to the treated-water tank 4. Therefore, a problem which might be caused by the structure as shown in FIG. 1 where the treated gas is circulated into biogas, can be prevented. That is, leakage of biogas via the treated-water drain 7 to the outside by a difference in pressure due to a back current of biogas to the circulation water tank 3, or leakage of treated gas via the treated-water drain 7 by the pressure of fan 8, can be prevented.

As described above, the apparatus for removing dissolved hydrogen sulfide in Example 1 includes an anaerobic treatment tank 1, a circulation water tank 3 that circulates a solution between itself and the anaerobic treatment tank 1 by a circulation pump 2, a treated-water tank 4 that temporarily stores anaerobically treated water discharged from the circulation water tank 3, a biological desulfurization tower 5 that desulfurizes biogas, an aeration tube 9a that blows a part of biologically desulfurized gas from the biological desulfurization tower 5, into the treated-water tank 4, and an aeration tube 9b that blows exhaust gas from the treated-water tank 4 into the circulation water tank 3, and the apparatus is constituted such that organic discharged water is introduced into circulation water, and simultaneously air and water are fed to the biological desulfurization tower 5.

According to Example 1, there is brought about the following effect:

That is, a part of the treated gas in the biological desulfurization tower 5 is blown into the treated-water tank 4, its exhaust gas is blown into the circulation water tank 3, and its exhaust gas is returned to the biological desulfurization tower 5, whereby the concentration of hydrogen sulfide dissolved in the liquid phase in the anaerobic treatment tank 1 can be reduced, and a reduction of the activity of anaerobic microorganisms by hydrogen sulfide can be prevented. Accordingly, the anaerobic treatment performance can be kept high.

For the same reason, the hydrogen sulfide concentration of anaerobically treated water can be reduced, and the treated water can be prevented from generating a bad smell.

For the same reason, the concentration of remaining oxygen in the treated gas in the biological desulfurization tower 5 is reduced, thereby increasing the methane concentration of the treated gas, and the amount of energy per unit flow volume of biogas can be increased.

EXAMPLE 2

Figure 2:
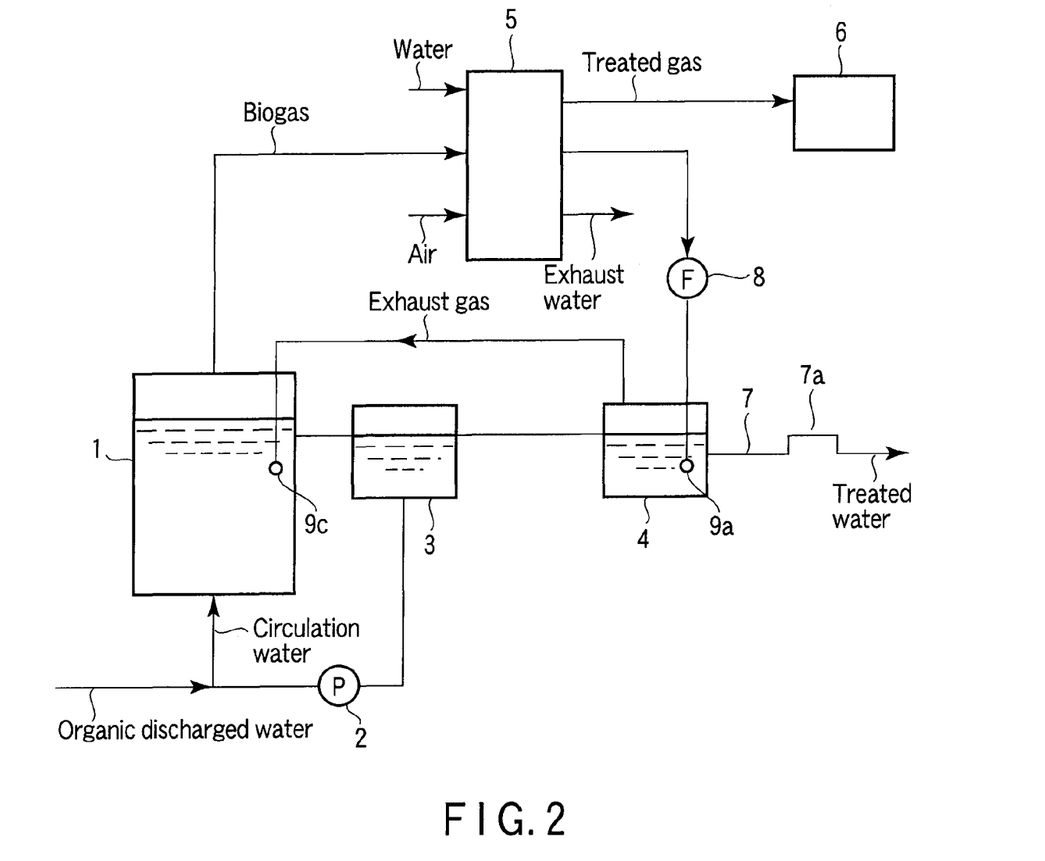
FIG. 2 is a block diagram of the apparatus for removing dissolved hydrogen sulfide in an anaerobic treatment in Example 2 according to the present invention.

FIG. 2 is a schematic block diagram of the apparatus for removing dissolved hydrogen sulfide in an anaerobic treatment in Example 2 according to the present invention. The same members as in FIG. 1 are assigned like numerals to omit their description.

The apparatus for removing dissolved hydrogen sulfide in Example 2 is different from that in Example 1 in that while exhaust gas from the treated-water tank 4 is blown into the circulation water tank 3 in the apparatus in Example 1, exhaust gas from the treated-water tank 4 is blown into the anaerobic treatment tank 1 via an aeration tube (second aerating means) 9c.

As shown in FIG. 2, the apparatus for removing dissolved hydrogen sulfide in Example 2 includes an anaerobic treatment tank 1, a circulation water tank 3 that circulates a solution between itself and the anaerobic treatment tank 1 by a circulation pump 2, a treated-water tank 4 that temporarily stores anaerobically treated water discharged from the circulation water tank 3, a biological desulfurization tower 5 that desulfurizes biogas, an aeration tube 9a that blows a part of biologically desulfurized gas from the biological desulfurization tower 5, into the treated-water tank 4, and an aeration tube 9c that blows exhaust gas from the treated-water tank 4 into the anaerobic treatment tank 1, and the apparatus is constituted such that organic discharged water is introduced into circulation water, and simultaneously air and water are fed to the biological desulfurization tower 5.

According to Example 2, there is brought about the following effect:

That is, a part of the treated gas in the biological desulfurization tower 5 is blown into the treated-water tank 4, and its exhaust gas is blown into the anaerobic treatment tank 1, whereby the concentration of hydrogen sulfide dissolved in the liquid phase in the anaerobic treatment tank 1 can be reduced, and a reduction in the activity of anaerobic microorganisms by hydrogen sulfide can be prevented. Accordingly, the anaerobic treatment performance can be kept high.

For the same reason, the hydrogen sulfide concentration of anaerobically treated water can be reduced, and the treated water can be prevented from generating a bad smell. For the same reason, the concentration of remaining oxygen in the treated gas in the biological desulfurization tower 5 is reduced, thereby increasing the methane concentration of the treated gas, and the amount of energy per unit flow volume of biogas can be increased.

EXAMPLE 3

Figure 3:
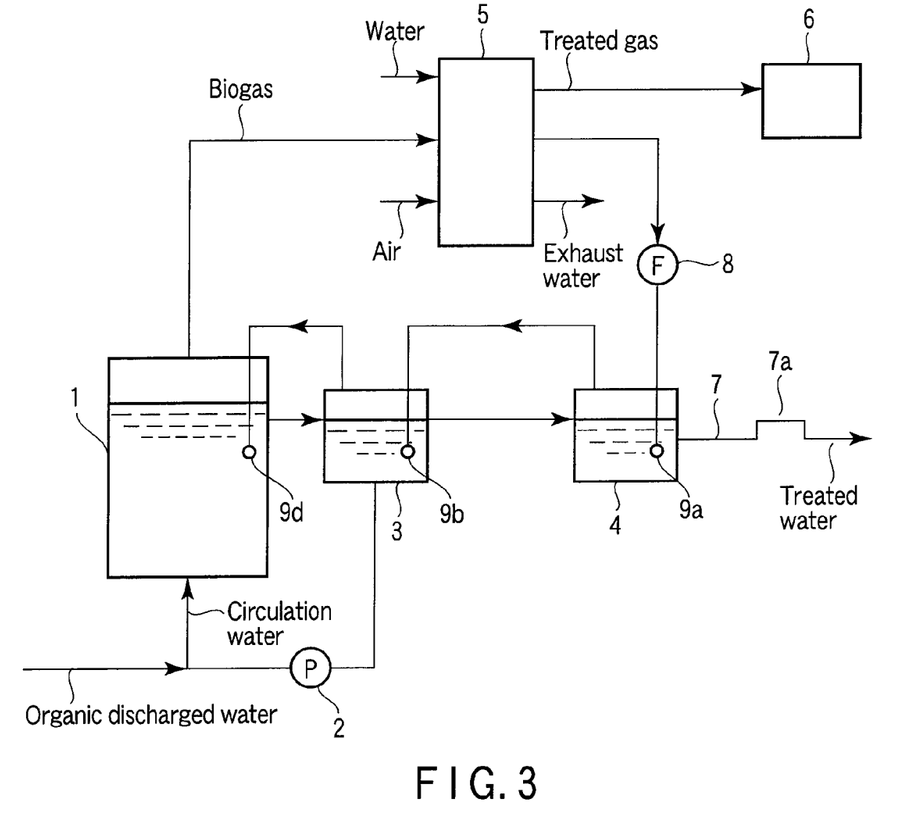
FIG. 3 is a block diagram of the apparatus for removing dissolved hydrogen sulfide in an anaerobic treatment in Example 3 according to the present invention.

FIG. 3 is a schematic block diagram of the apparatus for removing dissolved hydrogen sulfide in an anaerobic treatment in Example 3 according to the present invention. The same members as in FIGS. 1 and 2 are assigned like numerals to omit their description.

The apparatus in Example 1 is constituted such that exhaust gas from the treated-water tank 4 is blown into the circulation water tank 3. In the apparatus for removing dissolved hydrogen sulfide in Example 3, on the other hand, the second aerating means is composed of an aeration tube 9b that blows exhaust gas from the treated-water tank 4 into the circulation water tank 3 and an aeration tube 9d that blows exhaust gas from the circulation water tank 3 into the anaerobic treatment layer 1. The second aerating means is constituted of the aeration tubes 9b and 9d.

As shown in FIG. 3, the apparatus for removing dissolved hydrogen sulfide in Example 3 includes an anaerobic treatment tank 1, a circulation water tank 3 that circulates a solution between itself and the anaerobic treatment tank 1 by a circulation pump 2, a treated-water tank 4 that temporarily stores anaerobically treated water discharged from the circulation water tank 3, a biological desulfurization tower 5 that desulfurizes biogas, an aeration tube 9a that blows a part of biologically desulfurized gas from the biological desulfurization tower 5 into the treated-water tank 4, an aeration tube 9b that blows exhaust gas from the treated-water tank 4 into the circulation water tank 3, and an aeration tube 9d that blows exhaust gas from the circulation water tank 3 into the anaerobic treatment tank 1, and the apparatus is constituted such that organic discharged water is introduced into circulation water, and simultaneously air and water are fed to the biological desulfurization tower 5.

According to Example 3, there is brought about the following effect:

That is, a part of the treated gas in the biological desulfurization tower 5 is blown into the treated-water tank 4, its exhaust gas is blown into the circulation water tank 3, and exhaust gas from the circulation water tank 3 is blown into the anaerobic treatment tank 1, whereby the concentration of hydrogen sulfide dissolved in the liquid phase in the anaerobic treatment tank 1 can be reduced, and a reduction in the activity of anaerobic microorganisms by hydrogen sulfide can be prevented. Accordingly, the anaerobic treatment performance can be kept high.

For the same reason, the hydrogen sulfide concentration of anaerobically treated water can be reduced, and the treated water can be prevented from generating a bad smell. For the same reason, the concentration of remaining oxygen in the treated gas in the biological desulfurization tower 5 is reduced, thereby increasing the methane concentration of the treated gas, and the amount of energy per unit flow volume of biogas can be increased.

EXAMPLE 4

Figure 4:
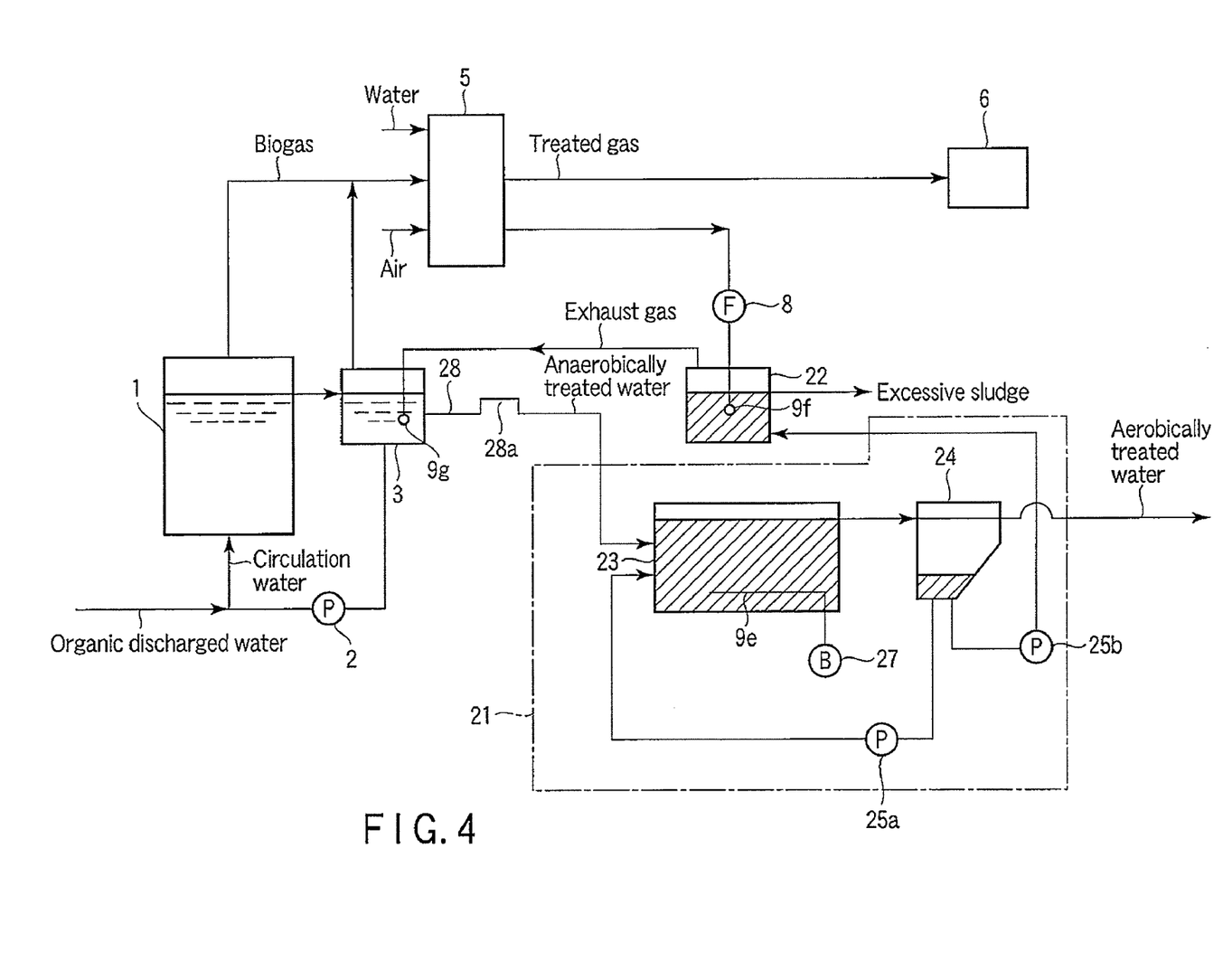
FIG. 4 is a block diagram of the apparatus for removing dissolved hydrogen sulfide in an anaerobic treatment in Example 4 according to the present invention.

FIG. 4 is a schematic block diagram of the apparatus for removing dissolved hydrogen sulfide in an anaerobic treatment in Example 4 according to the present invention. The same members as in FIGS. 1 and 2 are assigned like numerals to omit their description.

Numeral 21 in the figure refers to aerobic treatment means for aerobically treating anaerobically treated water by the active sludge process. Numeral 22 is a sludge storage tank that temporarily stores excessive sludge generated by aerobic treatment. The aerobic treatment means 21 includes a reaction tank 23 that aerobically treats anaerobically treated water by the action of active sludge, a depositing reservoir 24 that separates aerobically treated water from active sludge, a sludge returning pump 25a, a sludge drawing pump 25b, and a blower 27 that diffuses air through an aeration tube 9e in the reaction tank 23. The sludge returning pump 25a is that which returns sludge at the bottom of the depositing reservoir 24 to the reaction tank 23. The sludge drawing pump 25b is that which sends sludge at the bottom of the depositing reservoir 24 to the sludge storage tank 22. Numeral 9f in the figure is an aeration tube arranged in the sludge storage tank 22, and numeral 9g is an aeration tube arranged in the circulation water tank 3.

In the thus constituted apparatus for removing dissolved hydrogen sulfide, a part of biologically desulfurized gas from the biological desulfurization tower 5 is blown by fan 8 via the aeration tube 9f into the sludge storage tank 22. By so doing, oxygen in the treated gas is consumed with sludge in an anaerobic state. Exhaust gas from the sludge storage tank 22 is blown via the aeration tube 9f into the circulation water tank 3. By so doing, oxygen is not brought into the circulation water tank 3.

On the other hand, a water seal portion 28a is arranged in an anaerobic treatment water pipe 28 from the circulation water tank 3. Sludge from the depositing reservoir 24 is returned to the reaction tank 23 by the sludge returning pump 25a and simultaneously returned to the sludge storage tank 22 by the sludge drawing pump 25b. Excessive sludge in the sludge storage tank 22 is taken to the outside. Aerobically treated water from the depositing reservoir 24 is taken to the outside.

According to Example 4, there is brought about the following effect:

That is, a part of the treated gas in the biological desulfurization tower 5 is blown into the sludge storage tank 22, and thus oxygen in the treated gas is consumed with sludge in an anaerobic state. Exhaust gas from the sludge storage tank 22 is blown through the aeration tube 9g into the circulation water tank 3, and thus oxygen is not brought into the circulation water tank 3. Further, anaerobically treated water from the circulation water tank 3 is water-sealed with the water seal portion 28a in the anaerobic treatment water pipe 28, and aerobically treated water from the reaction tank 23 passes through the depositing reservoir 24 and is discharged to the outside. It follows that like Example 1, the anaerobic treatment performance can be kept high, the treated water can be prevented from generating a bad smell, and the amount of energy per unit flow volume of biogas can be increased.

EXAMPLE 5

Figure 5:
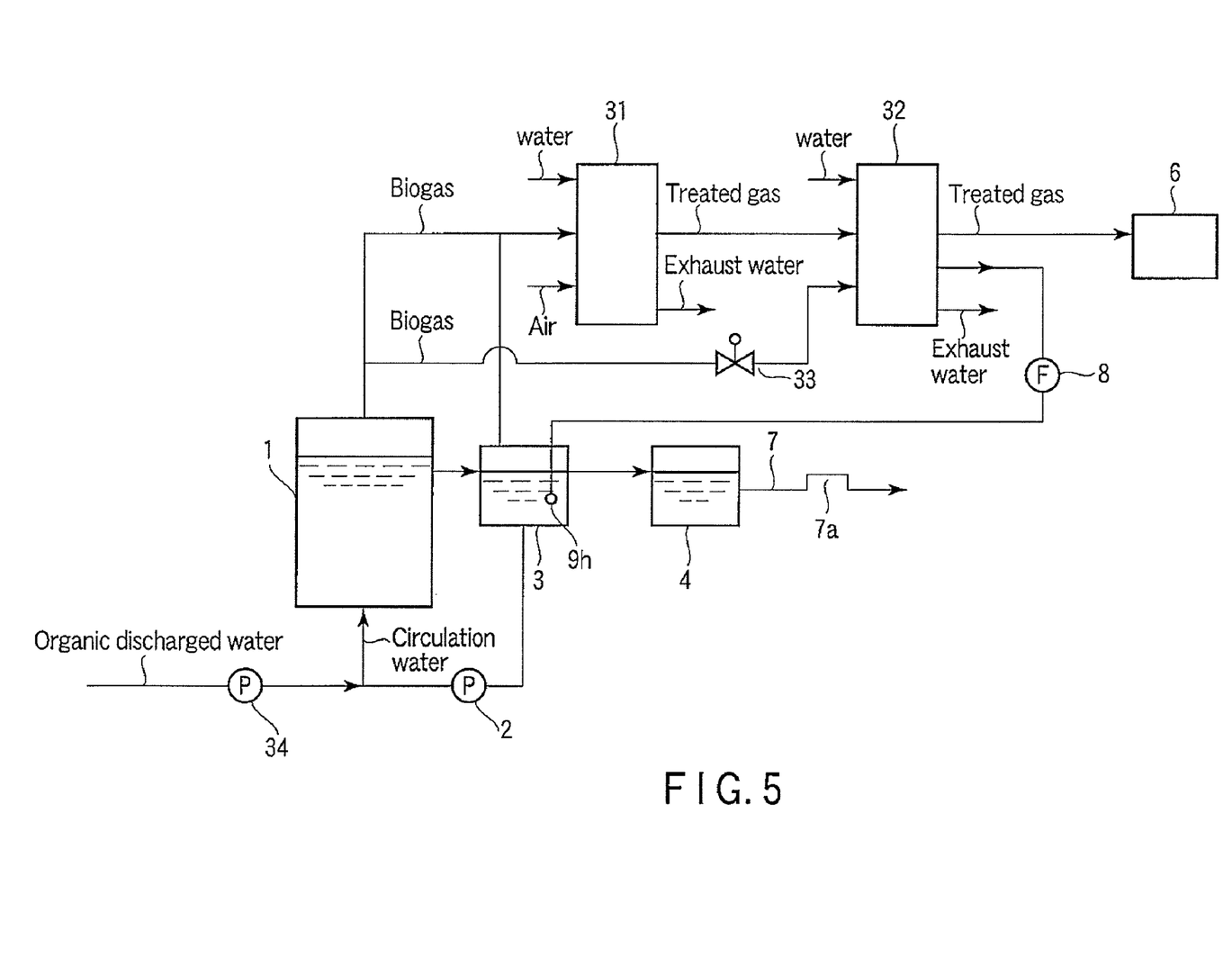
FIG. 5 is a block diagram of the apparatus for removing dissolved hydrogen sulfide in an anaerobic treatment in Example 5 according to the present invention.

FIG. 5 is a schematic block diagram of the apparatus for removing dissolved hydrogen sulfide in an anaerobic treatment in Example 5 according to the present invention. The same members as in FIGS. 1 and 2 are assigned like numerals to omit their description.

Numeral 31 in the figure refers to a first biological desulfurization tower that desulfurizes biogas formed in an anaerobic treatment tank 1. Numeral 32 refers to a second biological desulfurization tower to which treated gas and biogas from the first biological desulfurization tower 31 are sent and which desulfurizes the biogas. A part of the treated gas from the second biological desulfurization tower 32 is blown via an aeration tube 9h. Numeral 33 refers to a flow control valve for controlling the flow rate of biogas fed from the anaerobic treatment tank 1 to the second biological desulfurization tower 32. Numeral 34 refers to a feed pump for sending organic discharged water to circulation water. Because the second biological desulfurization tower 32 is supplied with biogas at such a flow rate as to consume oxygen in the treated gas from the first biological desulfurization tower 31, there is almost no oxygen in the second biological desulfurization tower 32. The concentration of oxygen in the treated gas from the first biological desulfurization tower 31 can be determined by analyzing the treated gas collected therefrom. The flow rate of biogas at which oxygen in the treated gas is consumed can be determined stoichiometrically by the concentration of hydrogen sulfide determined by analyzing the concentration of hydrogen sulfide in the biogas collected therefrom and by the concentration of oxygen in the treated gas.

As shown in FIG. 5, the apparatus for removing dissolved hydrogen sulfide in Example 5 is provided in tandem with the first biological desulfurization tower 31 and the second biological desulfurization tower 32. It follows that by the apparatus similar to that in Example 1, the anaerobic treatment performance can be kept high, the treated water can be prevented from generating a bad smell, and the amount of energy per unit flow volume of biogas can be increased, and further, almost no oxygen is left in the treated gas from the second biological desulfurization tower 32.

The invention claimed is:

1. An apparatus for removing dissolved hydrogen sulfide in an anaerobic treatment, characterized by comprising:
   an anaerobic treatment tank that anaerobically treats organic discharged water;
   a circulation water tank that circulates a solution between itself and the anaerobic treatment tank by a circulation pump;
   means for introducing organic discharged water into circulation water circulating between the anaerobic treatment tank and the circulation water tank;
   a treated-water tank that temporarily stores anaerobically treated water discharged from the circulation water tank;
   a biological desulfurization tower that desulfurizes biogas formed by anaerobic treatment;
   air feeding means for feeding air to the biological desulfurization tower;
   water feeding means for feeding water to the biological desulfurization tower;
   first aerating means for blowing a part of biologically desulfurized gas from the biological desulfurization tower, into the treated-water tank; and
   second aerating means for blowing exhaust gas discharged from the treated-water tank into a solution circulating between the anaerobic treatment tank and the circulation water tank.

2. The apparatus for removing dissolved hydrogen sulfide in an anaerobic treatment according to claim 1, characterized in that the second aerating means is aerating means for blowing exhaust gas discharged from the treated-water tank into the circulation water tank.

3. The apparatus for removing dissolved hydrogen sulfide an anaerobic treatment according to claim 2, which comprises means for returning exhaust gas discharged from the circulation water tank to the biological desulfurization tower.

4. The apparatus for removing dissolved hydrogen sulfide in an anaerobic treatment according to claim 1, characterized in that the second aerating means is aerating means for blowing exhaust gas discharged from the treated-water tank into the anaerobic treatment tank.

5. The apparatus for removing dissolved hydrogen sulfide in an anaerobic treatment according to claim 1, characterized in that the second aerating means consists of aerating means for blowing exhaust gas discharged from the treated-water tank into the circulation water tank and aerating means for blowing exhaust gas discharged from the circulation water tank into the anaerobic treatment tank.

6. An apparatus for removing dissolved hydrogen sulfide in an anaerobic treatment, characterized by comprising an anaerobic treatment tank that anaerobically treats organic discharged water, a circulation water tank that circulates a solution between itself and the anaerobic treatment tank by a circulation pump, means for introducing organic discharged water into circulation water circulating between the anaerobic treatment tank and the circulation water tank, a biological desulfurization tower that desulfurizes biogas formed by anaerobic treatment, air feeding means for feeding air to the biological desulfurization tower, water feeding means for feeding water to the biological desulfurization tower, means for aerobically treating anaerobically treated water, a sludge storage tank that temporarily stores excessive sludge generated by aerobic treatment, aerating means for blowing a part of biologically desulfurized gas from the biological desulfurization tower into the sludge storage tank, aerating means for blowing exhaust gas discharged from the sludge storage tank into the circulation water tank, and means for returning exhaust gas discharged from the circulation water tank to the biological desulfurization tower.

7. An apparatus for removing dissolved hydrogen sulfide in an anaerobic treatment, characterized by comprising an anaerobic treatment tank that anaerobically treats organic discharged water, a circulation water tank that circulates a solution between itself and the anaerobic treatment tank by a circulation pump, means for introducing organic discharged water into circulation water circulating between the anaerobic treatment tank and the circulation water tank, a treated-water tank that temporarily stores anaerobically treated water discharged from the circulation water tank, a first biological desulfurization tower that desulfurizes biogas formed by anaerobic treatment, air feeding means for feeding air to the first biological desulfurization tower, water feeding means for feeding water to the first biological desulfurization tower, a second biological desulfurization tower to which treated gas and biogas from the first biological desulfurization tower are sent and which desulfurizes the biogas, water feeding means for feeding water to the second biological desulfurization tower, aerating means for blowing a part of treated gas from the second biological desulfurization tower into the circulation water tank, and means for returning exhaust gas discharged from the circulation water tank to the biological desulfurization tower.

* * * * *